(12) United States Patent
Liao et al.

(10) Patent No.: US 8,703,949 B2
(45) Date of Patent: Apr. 22, 2014

(54) TANDEM PROCESS FOR PREPARING N-ALKYL MORPHINANS

(75) Inventors: Subo Liao, Ballwin, MO (US); Peter X. Wang, Creve Coeur, MO (US); David W. Berberich, St. Peters, MO (US); Douglas C. Miller, University City, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 195 days.

(21) Appl. No.: 13/196,921

(22) Filed: Aug. 3, 2011

(65) Prior Publication Data

US 2012/0035367 A1 Feb. 9, 2012

Related U.S. Application Data

(60) Provisional application No. 61/370,628, filed on Aug. 4, 2010.

(51) Int. Cl.

| | | |
|---|---|---|
| *C07D 489/00* | (2006.01) | |
| *C07D 221/22* | (2006.01) | |
| *C07D 221/28* | (2006.01) | |
| *A61K 31/44* | (2006.01) | |
| *C07D 211/00* | (2006.01) | |
| *C07D 213/00* | (2006.01) | |
| *C07D 215/00* | (2006.01) | |
| *C07D 217/00* | (2006.01) | |
| *C07D 219/00* | (2006.01) | |
| *C07D 221/00* | (2006.01) | |
| *C07D 471/00* | (2006.01) | |
| *C07D 491/00* | (2006.01) | |
| *C07D 498/00* | (2006.01) | |
| *C07D 513/00* | (2006.01) | |
| *C07D 515/00* | (2006.01) | |
| *C07D 489/08* | (2006.01) | |

(52) U.S. Cl.
USPC .......... 546/44; 546/15; 546/45; 546/46; 546/74; 514/278; 514/282; 514/289

(58) Field of Classification Search
CPC .. C07D 489/00; C07D 221/22; C07D 221/28; A61K 31/44
See application file for complete search history.

(56) References Cited

U.S. PATENT DOCUMENTS

2009/0156815 A1    6/2009  Wang et al.

FOREIGN PATENT DOCUMENTS

| EP | 1857435 | 11/2007 |
|---|---|---|
| WO | 2009003270 | 1/2009 |
| WO | 2009079013 | 6/2009 |
| WO | 2009122436 | 10/2009 |
| WO | 2009154673 | 12/2009 |

OTHER PUBLICATIONS

Carey, FA. Organic Chemistry 6th Ed. McGraw Hill. 2006, chapter 1, p. 50, last paragraph of section 1.17.*
Lundberg, P. et al. Click Assisted One-Pot Multi-Step Reactions in Polymer Science: Accelerated Synthetic Protocols. Macromolecular Rapid Communications. 2008, vol. 29, p. 1001, left column, lines 4-5, right column, "Click Chemistry".*
Lundberg, P. et al. Click Assisted One-Pot Multi-Step Reactions in Polymer Science: Accelerated Synthetic Protocols. Macromolecular Rapid Communications. 2008, vol. 29, p. 1001.*
Mayr, H. et al. Scales of Nucleophilicity and Electrophilicity: A system for Ordering Polar Organic and Organometallic Reactions. Angew. Chem. Int. Ed. Engl. 1994, vol. 33, p. 940.*
Dorwold, FZ. Side Reactions in Organic Synthesis. Wiley. 2005, preface.*
Schmidhamm ER, H. et al. Synthesis and Biological Evaluation of 14-Alkoxymorphinans. 3. Extensive Study on Cyprodime-Related Compounds. J. Med. Chem. 1990, vol. 33, p. 1206.*
Chen, C. et al. A Facile Synthesis and Structural Verification of Etorphine and Dihydroetorphine from Codeine. Journal of the Chinese Chemical Society. 2011, vol. 58, p. 104.*
Csutoras et al. (2004) "An investigation of the N-demethylation of 3-deoxymorphine and the affinity of the alkylation products" 12, pp. 2687-2690.
Judd et al (1992) "Synthesis, Antinociceptive Activity, and °plaid Receptor Profiles" 35, pp. 48-56.

\* cited by examiner

*Primary Examiner* — Rita Desai
*Assistant Examiner* — Ben S Michelson

(57) ABSTRACT

The present invention provides processes for the preparation of N-alkyl morphinans without the isolation of nor-morphinan intermediates. In particular, the invention provides tandem hydrolysis/alkylation reactions for the synthesis of N-alkyl morphinans.

15 Claims, No Drawings

TANDEM PROCESS FOR PREPARING N-ALKYL MORPHINANS

CROSS REFERENCE TO RELATED APPLICATIONS

This application claims the benefit of U.S. Provisional Application No. 61/370,628 filed Aug. 4, 2010, which is incorporated herein in its entirety.

FIELD OF THE INVENTION

The present invention generally relates to the preparation of N-alkyl morphinans without the isolation of nor-morphinan intermediates.

BACKGROUND OF THE INVENTION

N-alkyl morphinans such as naltrexone, nalbuphine, naloxone, nalmefene, and buprenorphine are important narcotic pharmaceuticals. The current processes for preparing N-alkyl morphinans comprise several separate steps in which the nor-morphinan intermediate is always isolated and then reacted with an N-alkylating reagent to form the N-alkyl morphinan. Because nor-morphinans are very water soluble, multiple extractions are typically needed to minimize loss of the nor-morphinan intermediate. Consequently, these isolation processes often take a long time, sometimes, even days to separate the organic and aqueous phases. What is needed, therefore, is a streamlined, cost-effective process in which N-alkyl morphinans can be prepared in less time, with less effort, and in high yield.

SUMMARY OF THE INVENTION

The present invention provides processes for preparing N-alkyl morphinans from N-hydrocarboxycarbonyl morphinans via tandem hydrolysis/alkylation reactions.

Briefly, therefore, one aspect of the present invention encompasses a process for preparing an N-alkyl morphinan from an N-hydrocarboxycarbonyl morphinan. The process comprises contacting the N-hydrocarboxycarbonyl morphinan with a nucleophile to form a nor-morphinan, and then contacting the nor-morphinan with carbon dioxide gas followed by an N-alkylating agent to form the N-alkyl morphinan.

Another aspect of the invention provides a process for preparing a compound comprising Formula (IV) from a compound comprising Formula (II). The process comprises (a) contacting the compound comprising Formula (II) with a nucleophile to form a compound comprising Formula (III), and (b) contacting the compound comprising Formula (III) with carbon dioxide gas followed by an N-alkylating agent comprising $R^{17}X$ to form the compound comprising Formula (IV) according to the following reaction scheme:

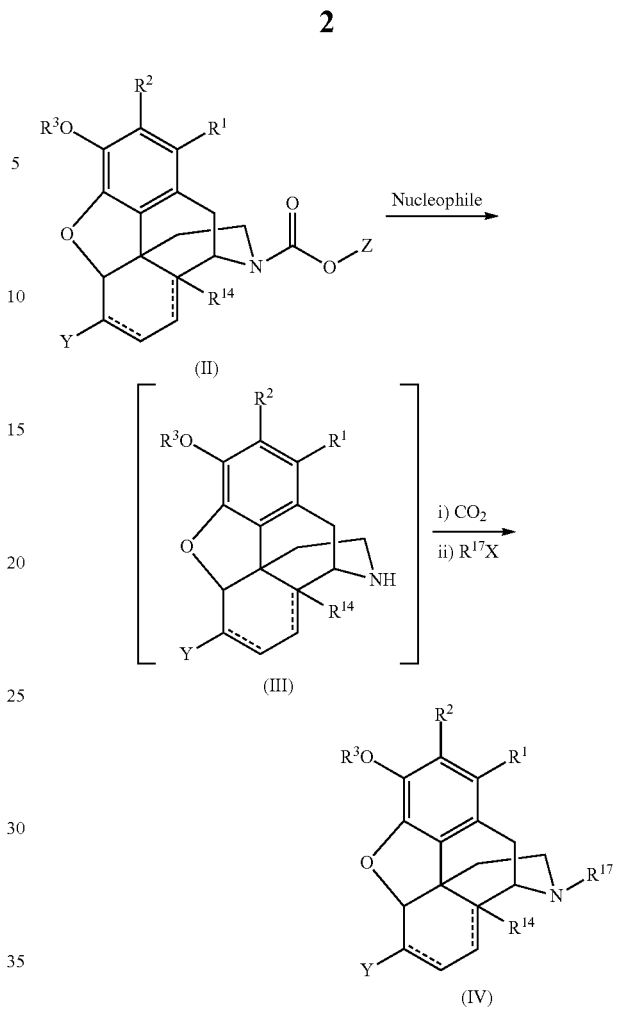

wherein:

$R^1$ and $R^2$ are independently chosen from hydrogen, halogen, hydroxy, amino, cyano, {—}$OR^8$, hydrocarbyl, and substituted hydrocarbyl;

$R^3$ is chosen from hydrogen, hydrocarbyl, and substituted hydrocarbyl;

$R^{14}$ is chosen from hydrogen, halogen, hydroxy, {—}$OR^8$, hydrocarbyl, and substituted hydrocarbyl;

$R^8$, $R^{17}$ and Z are independently chosen from hydrocarbyl and substituted hydrocarbyl;

X is a leaving group; and

Y is chosen from hydroxy, alkoxy, aryloxy, and acetal, wherein each dashed line indicates an optional double bond.

A further aspect of the invention encompasses a process for preparing a compound comprising Formula (IV) from a compound comprising Formula (I). The process comprises a) contacting the compound comprising Formula (I) with an N-demethylating agent comprising LC(O)OZ and a proton acceptor to form a compound comprising Formula (II); (b) contacting the compound comprising Formula (II) with a nucleophile to form a compound comprising Formula (III); and (c) contacting the compound comprising Formula (III) with carbon dioxide gas followed by an N-alkylating agent comprising $R^{17}X$ to form the compound comprising Formula (IV) according to the following reaction scheme:

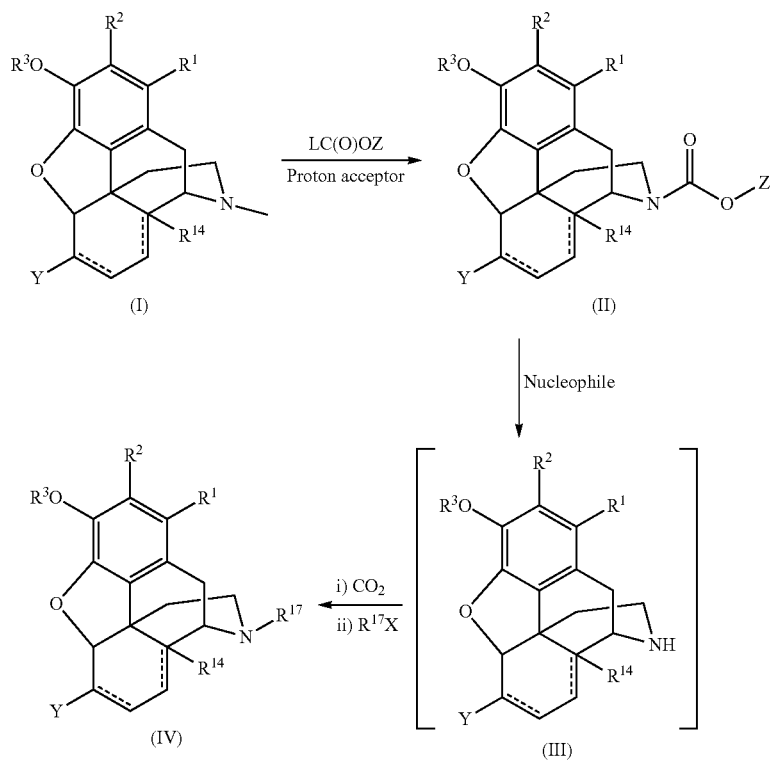

wherein:
R[1] and R[2] are independently chosen from hydrogen, halogen, hydroxy, amino, cyano, {—}OR[8], hydrocarbyl, and substituted hydrocarbyl;
R[3] is chosen from hydrogen, hydrocarbyl, and substituted hydrocarbyl;
R[14] is chosen from hydrogen, halogen, hydroxy, {—}OR[8], hydrocarbyl, and substituted hydrocarbyl;
R[8], R[17] and Z are independently chosen from hydrocarbyl and substituted hydrocarbyl;
L is halogen;
X is a leaving group; and
Y is chosen from hydroxy, alkoxy, aryloxy, and acetal, wherein each dashed line indicates an optional double bond.

Other features and iterations of the invention are described in more detail below.

DETAILED DESCRIPTION OF THE INVENTION

Disclosed herein is an efficient synthetic process for preparing N-alkyl morphinans from N-methyl morphinans. In particular, the N-methyl morphinan is demethylated into an N-hydrocarboxycarbonyl morphinan, which is then hydrolyzed into a nor-morphinan. Importantly, the nor-morphinan intermediate is not isolated and is directly reacted in situ with an N-alkylating agent to form the N-alkyl morphinan. The N-alkyl morphinan, therefore, is prepared from the N-hydrocarboxycarbonyl morphinan using tandem hydrolysis/alkylation reactions. Since this new tandem process is conducted in one pot, there is a significant reduction in process time and effort.

(I) Processes for the Preparation of N-Alkyl Morphinans

One aspect of the invention encompasses a process for the synthesis of an N-alkyl morphinan from an N-hydrocarboxycarbonyl morphinan. The processes comprise contacting the N-hydrocarboxycarbonyl morphinan with a nucleophile to form a nor-morphinan, and contacting the nor-morphinan with carbon dioxide gas followed by an N-alkylating agent to form the N-alkyl morphinan. Advantageously, the two steps of the process may be conducted in tandem in a single pot, without isolating the nor-morphinan intermediate.

In general, the morphinans detailed herein include any compound comprising a morphinan structure as diagrammed below. For the purposes of illustration, the ring atoms of the core morphinan structure are numbered as diagrammed below, wherein R is hydrogen, hydrocarbyl or substituted hydrocarbyl:

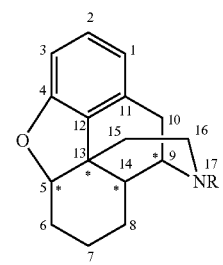

Morphinan compounds have asymmetric centers. In particular, the core morphinan compound may have at least four chiral carbons (designated by asterisks); namely, C-5, C-13, C-14, and C-9.

(II) Processes for the Preparation of Compounds Comprising Formula (IV) from Compounds Comprising Formula (I)

In another embodiment of the invention, an N-alkyl morphinan comprising Formula (IV) is prepared from an N-methyl morphinan comprising Formula (I). The process comprises contacting the compound comprising Formula (I) with an N-demethylating agent comprising LC(O)OZ and a proton acceptor to form an N-hydrocarboxycarbonyl morphinan comprising Formula (II). The compound comprising Formula (II) is hydrolyzed by contact with a nucleophile to form a nor-morphinan comprising Formula (III). The process further comprises contacting the compound comprising Formula (III) with carbon dioxide gas followed by an N-alkylating agent comprising $R^{17}X$ to form the compound comprising Formula (IV). An advantage of the process is that the alkylation step can directly follow the hydrolysis step without isolating the intermediate compound comprising Formula (III). For purposes of illustration, Reaction Scheme 1 depicts the synthesis of the compound comprising Formula (IV) in accordance with this aspect of the invention:

Reaction Scheme 1:

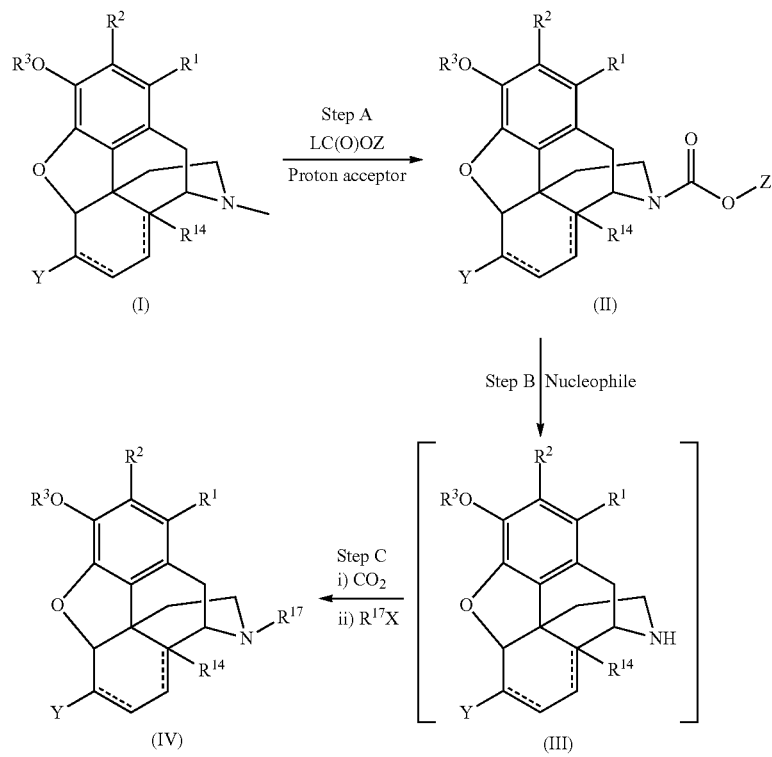

wherein:
$R^1$ and $R^2$ are independently chosen from hydrogen, halogen, hydroxy, amino, cyano, {—}$OR^8$, hydrocarbyl, and substituted hydrocarbyl;
$R^3$ is chosen from hydrogen, hydrocarbyl, and substituted hydrocarbyl;
$R^{14}$ is chosen from hydrogen, halogen, hydroxy, {—}$OR^8$, hydrocarbyl, and substituted hydrocarbyl;
$R^8$, $R^{17}$ and Z are independently chosen from hydrocarbyl and substituted hydrocarbyl;
L is halogen;
X is a leaving group; and
Y is chosen from hydroxy, alkoxy, aryloxy, and acetal, wherein each dashed line indicates an optional double bond.

In one embodiment, $R^1$, $R^2$, and $R^{14}$ are independently chosen from hydrogen, halogen, hydroxyl, alkyoxy, acyl, alkyl, alkenyl, aryl, substituted alkyl, substituted alkenyl, substituted aryl, alkoxycarbonyl, and aroxycarbonyl. In a preferred embodiment, $R^1$ and $R^2$ are hydrogen, and $R^{14}$ is hydrogen, hydroxyl, or protected hydroxyl. In another embodiment, $R^3$ is chosen from hydrogen, alkyl, alkenyl, aryl, substituted alkyl, substituted alkenyl, substituted aryl, acyl, alkoxycarbonyl, aroxycarbonyl, acetal, ether, silyl ether, and alkylsulfonyl. Preferably, $R^3$ is hydrogen, methyl, or an oxygen protecting group. In still another embodiment, $R^{17}$ is chosen from alkyl, alkenyl, alkylaryl, aralkyl, aryl, substituted alkyl, substituted alkenyl, substituted alkylaryl, substituted aralkyl, and substituted aryl. Preferred $R^{17}$ groups include methyl, ethyl, propyl, cyclopropyl, cyclopropylmethyl, butyl, isobutyl, t-butyl, cyclobutyl, cyclobutylmethyl, pentyl, isopenyl, neopentyl, cyclopenyl, benzyl, and allyl. In a further embodiment, X is halogen or $SO_2OR$, wherein R is alkyl, aryl, substituted alkyl, or substituted aryl. In yet another embodiment, Y is methoxy, ethoxy, or ethylene acetal. In an alternate embodiment, Z is chosen from alkyl, alkenyl, alkylaryl, aralkyl, aryl, substituted alkyl, substituted alkenyl, substituted alkylaryl, substituted aralkyl, and substituted aryl. Preferred Z groups include alkyl, methyl, ethyl, propyl, isopropyl, butyl, isobutyl, tert-butyl, phenyl, benzyl, methoxymethyl, vinyl, and 2-chloroethyl. Even more preferred Z groups are alkyl and phenyl.

In a preferred embodiment, $R^1$ and $R^2$ are hydrogen; $R^3$ is hydrogen, methyl, or an oxygen protecting group; $R^{14}$ is hydrogen, hydroxy, or protected hydroxy; $R^{17}$ is ethyl, allyl, benzyl, cyclopropylmethyl, or cyclobutylmethyl; X is halogen; Y is methoxy, ethoxy, or ethylene acetal; and Z is alkyl or phenyl.

(a) Step A of the Process

The process commences with formation of a reaction mixture by combining the compound comprising Formula (I)

with an N-demethylating agent comprising LC(O)OZ and a proton acceptor. The components of the reaction mixture and the reaction conditions of this step of the process are described below.

(i) N-Demethylating Agent Comprising LC(O)OZ

A variety of N-demethylating agents are suitable for use in the process of the invention. In general, the N-demethylating agent will be a hydrocarbyl haloformate having the formula LC(O)OZ, wherein L and Z are as defined above. In a preferred embodiment, L may be chloro or bromo, and Z may be methyl, ethyl, propyl, isopropyl, butyl, isobutyl, tert-butyl, phenyl, benzyl, methoxymethyl, vinyl, or 2-chloroethyl. In preferred embodiments, the N-demethylating agent may be an alkyl haloformate (e.g., methyl chloroformate, methyl bromoformate, ethyl chloroformate, ethyl bromoformate, propyl chloroformate, propyl bromoformate, isopropyl chloroformate, isopropyl bromoformate, butyl chloroformate, butyl bromoformate, isobutyl chloroformate, isobutyl bromoformate, and the like), an alkoxyalkyl haloformate (e.g., methyoxymethyl chloroformate, methyoxymethyl bromoformate, ethoxymethyl chloroformate, ethoxymethyl bromoformate, and so forth), benzyl haloformate, phenyl haloformate, vinyl haloformate, or 2-chloroalkyl haloformate. In general, the alkyl comprises from one to eight carbon atoms. In exemplary embodiments, the N-demethylating agent may be an alkyl chloroformate, phenyl chloroformate, benzyl chloroformate, vinyl chloroformate, or 2-chloroalkyl chloroformate.

The molar ratio of the compound comprising Formula (I) to the N-demethylating agent can and will vary depending. In general, the molar ratio of the compound comprising Formula (I) to the N-demethylating agent to may range from about 1:1 to about 1:3. In various embodiments, the molar ratio of the compound comprising Formula (I) to the N-demethylating agent may be about 1:1.0, 1:1.1, 1:1.2, 1:1.3, 1:1.4, 1:1.5, 1:1.6, 1:1.7: 1:1.8, 1:1.9, 1:2.0, 1:2.1, 1:2.2. 1:2.3, 1:2.4. 1:2.5, 1:2.6, 1:2.7, 1:2.8, 1:2.9, or 1:3.0. In an exemplary embodiment, the molar ratio of the compound comprising Formula (I) to the N-demethylating agent may be about 1:1.2.

(ii) Proton Acceptor

To facilitate the N-demethylation of the compound comprising Formula (I), the reaction is typically carried out in the presence of a proton acceptor. In general, the proton acceptor has a pKa of between about 7 and about 13, preferably between about 8 and about 10. Representative proton acceptors that may be employed include, but are not limited to, borate salts (such as, for example, $Na_3BO_3$), di- and tri-basic phosphate salts (such as, for example, $Na_2HPO_4$ and $Na_3PO_4$), bicarbonate salts (such as, for example, $NaHCO_3$, $KHCO_3$, mixtures thereof, and the like), hydroxide salts (such as, for example, NaOH, KOH, mixtures thereof, and the like), carbonate salts (such as, for example, $Na_2CO_3$, $K_2CO_3$, mixtures thereof, and the like), organic bases (such as, for example, pyridine, triethylamine, diisopropylethylamine, N-methylmorpholine, N,N-dimethylaminopyridine, and mixtures thereof), organic buffers (such as, for example, N-(2-acetamido)-2-aminoethane sulfonic acid (ACES), N-(2-acetamido)-iminodiacetic acid (ADA), N,N-bis(2-hydroxyethyl)glycine (BICINE), 3 (cyclohexylamino)-1-propanesulfonic acid (CAPS), 2 (cyclohexylamino) ethanesulfonic acid (CHES), 4-(2-hydroxyethyl)-1-piperazinepropanesulfonic acid (EPPS), 4-(2-hydroxyethyl) piperazine-1-ethanesulfonic acid (HEPES), 2 (4 morpholinyl) ethanesulfonic acid (MES), 4-morpholinepropanesulfonic acid (MOPS), 1,4-piperazinediethanesulfonic acid (PIPES), [(2-hydroxy-1,1-bis(hydroxymethyl)ethyl) amino]-1-propanesulfonic acid (TAPS), 2-[(2-hydroxy-1,1-bis(hydroxymethyl)ethyl)amino]ethanesulfonic acid (TES), salts and/or mixtures thereof, and the like), and combinations thereof. When the proton acceptor is an organic buffer, the organic buffer preferably lacks a hydroxy-substituted nitrogen atom, as this substituent may compete for reaction with a hydrocarbyl haloformate reactant. In one embodiment, the proton acceptor is chosen from $NaHCO_3$, $KHCO_3$, $K_2CO_3$, NaOH, KOH, and mixtures thereof. In a preferred embodiment, the proton acceptor is $NaHCO_3$, $KHCO_3$, or a combination thereof.

The molar ratio of the compound comprising Formula (I) to the proton acceptor may range from about 1:1 to about 1:6. In some embodiments, the molar ratio of the compound comprising Formula (I) to the proton acceptor may be about 1:1, 1:1.5, 1:2, 1:2.5, 1:3, 1:3.5, 1:4, 1:4.5, 1:5, 1:5.5, or 1:6. In a preferred embodiment, the molar ratio of the compound comprising Formula (I) to the proton acceptor may range from about 1:1.5 to about 1:3.

(iii) Solvent—Step A

The reaction is generally conducted in the presence of a solvent. The solvent may be a nonpolar organic solvent or a polar aprotic solvent. Representative nonpolar solvents include, but are not limited to, alkane and substituted alkane solvents (including cycloalkanes), aromatic hydrocarbons, esters, ethers, ketones, and combinations thereof. Specific nonpolar solvents that may be employed include, for example, benzene, butyl acetate, t-butyl methylether, t-butyl methylketone, chlorobenzene, chloroform, cyclohexane, dichloromethane, dichloroethane, diethyl ether, ethyl acetate, fluorobenzene, heptane, hexanes, isobutylmethylketone, methylethylketone, methylisobutyl ketone, pentyl acetate, propyl acetates, toluene, and combinations thereof. Non-limiting examples of suitable aprotic solvents include acetone, acetonitrile, diethoxymethane, N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMAC), N-methyl-2-pyrrolidinone (NMP), 1,4-dioxane, ethyl formate, formamide, hexachloroacetone, hexamethylphosphoramide, methyl acetate, N-methylacetamide, N-methylformamide, methylene chloride, methoxyethane, morpholine, nitrobenzene, nitromethane, propionitrile, sulfolane, tetramethylurea, tetrahydrofuran (THF), 2-methyl tetrahydrofuran, tetrahydropyran, trichloromethane, and combinations thereof. In an exemplary embodiment, the solvent may be chloroform, ethyl acetate, or acetonitrile.

In general, the molar ratio of the solvent to the compound comprising Formula (I) will range from about 0.5:1 to about 100:1. In various embodiments, the molar ratio of the solvent to the compound comprising Formula (I) may range from 0.5:1 to about 5:1, from about 5:1 to about 25:1, or from about 25:1 to about 100:1. In preferred embodiments, the molar ratio of the solvent to the compound comprising Formula (I) may range from about 0.5:1 to about 20:1. In an exemplary embodiment, the molar ratio of the solvent to the compound comprising Formula (I) may range from about 2:1 to about 10:1.

(iv) Reaction Conditions—Step A

In general, the reaction will be conducted at a temperature that ranges from about 0° C. to about 100° C., or more preferably from about 20° C. to about 60° C. In various embodiments, the demethylation reaction may be conducted at about 30° C., about 40° C., about 50° C., about 55° C., or about 60° C. The reaction is typically performed under ambient pressure, and preferably in an inert atmosphere (e.g., nitrogen or argon).

Typically, the reaction is allowed to proceed for a sufficient period of time until the reaction is complete, as determined by chromatography (e.g., HPLC). In this context, a "completed reaction" generally means that the reaction mixture contains a significantly diminished amount of the compound comprising Formula (I), and a significantly increased amount of the compound comprising Formula (II) compared to the amounts of each present at the beginning of the reaction. Typically, the amount of the compound comprising Formula (I) remaining in the reaction mixture after the reaction is complete may be less than about 3%, and preferably less than about 1%. In general, the reaction may proceed for about 1 hour to about 24 hours, and more typically, for about 2 hours to about 8 hours.

The compound comprising Formula (II) may be isolated from the reaction mixture using techniques known to those of skill in the art. Non-limiting examples of suitable techniques include precipitation, extraction, evaporation, distillation, chromatography, and crystallization.

The yield of the compound comprising Formula (II) can and will vary. Typically, the yield of the compound comprising Formula (II) may be at least about 65%. In one embodiment, the yield of the compound comprising Formula (II) may range from about 65% to about 75%. In another embodiment, the yield of the compound comprising Formula (II) may range from about 75% to about 85%. In a further embodiment, the yield of the compound comprising Formula (II) may range from about 85% to about 95%. In still another embodiment, the yield of the compound comprising Formula (II) may be greater than about 95%.

(b) Step B of the Process

The process further comprises contacting the compound comprising Formula (II) with a nucleophile such that the compound comprising Formula (II) is cleaved to form the compound comprising Formula (III). The reactants and reaction conditions of this step of the process are detailed below.

(i) Nucleophile

A variety of nucleophiles are suitable for use in this step of the process. In general, the nucleophile may have a pKa greater than about 13. Nucleophiles having this characteristic include hydroxides of alkali metals and alkaline earth metals (such as, for example, NaOH and $Ca(OH)_2$ and the like); alkoxides (such as, e.g., methoxide, ethoxide, and so forth); group 1 salts of carbanions (such as, e.g., methyl lithium, butyl lithium, and so forth); amides (such as, e.g., sodium amide, lithium methylamide, lithium isopropyl amide, and the like); and hydrides (such as, for example, sodium hydride, $NaBH_4$, and the like). In preferred embodiments, the nucleophile may be potassium hydroxide or sodium hydroxide.

The amount of nucleophile added to the reaction mixture can and will vary. In general, the molar ratio of the compound comprising Formula (II) to the nucleophile may range from about 1:1 to about 1:8. In various embodiments, the molar ratio of the compound comprising Formula (II) to the nucleophile may be about 1:1. 1:1.5, 1:2, 1:2.5, 1:3, 1:3.5, 1:4, 1:4.5, 1:5, 1:5.5, 1:6, 1:6.5, 1:7, 1:7.5, or 1:8.

(ii) Solvent—Steps B and C

The reaction mixture also comprises a solvent system. The solvent system preferably includes a nonpolar solvent. Representative nonpolar solvents are detailed above in section (II)(a)(iii). In preferred embodiments, the nonpolar solvent may be benzene, chloroform, diethyl ether, ethyl acetate, heptane, hexane, n-propyl acetate, toluene, or combinations thereof. In an exemplary embodiment, the nonpolar solvent may be toluene. The amount of nonpolar solvent added to the reaction mixture can and will vary. In general, the molar ratio of the nonpolar solvent to the compound comprising Formula (II) may range from about 0.5:1 to about 100:1. In one embodiment, the molar ratio of the nonpolar solvent to the compound comprising Formula (II) may range from about 1:1 to about 20:1. In a preferred embodiment, the molar ratio of the nonpolar solvent to the compound comprising Formula (II) may range from about 2:1 to about 10:1. In an exemplary embodiment, the molar ratio of the nonpolar solvent to the compound comprising Formula (II) may be about 4:1.

In some embodiments, the solvent system may further comprise a protic solvent. Non-limiting examples of suitable protic solvents include water, methanol, ethanol, isopropyl alcohol, isobutyl alcohol, t-butyl alcohol, n-propyl alcohol, n-butyl alcohol, and combinations thereof. The volume ratio of the protic solvent to the nonpolar solvent may range from about 1:1 to about 1:200, or more preferably from about 1:10 to about 1:100.

In still another embodiment, the solvent system may further comprise an aprotic solvent. Suitable aprotic solvents are presented above in section (II)(a)(iii). Preferred aprotic solvents include acetonitrile, 1-methyl-2-pyrrolidinone, N,N-dimethylacetamide, dimethyl sulfoxide, N,N-formamide, acetone, tetrahydrofuran, and combinations thereof. In an exemplary embodiment, the aprotic solvent may be dimethyl sulfoxide. The volume ratio of the aprotic solvent to the nonpolar solvent may range from about 1:1 to about 1:10, or more preferably about 1:5. In an exemplary embodiment, the solvent system comprises toluene and dimethyl sulfoxide.

(iii) Reaction Conditions—Step B

The reaction may be conducted at a temperature that ranges from about 0° C. to about 100° C., or more preferably from about 50° C. to about 90° C. In various embodiments, the temperature of the reaction may range from about 50-70° C., from about 70-80° C., from about 80-85° C., or from about 80-90° C. The reaction is typically performed under ambient pressure, and preferably in an inert atmosphere (e.g., nitrogen or argon).

Typically, the reaction is allowed to proceed for a sufficient period of time until the reaction is complete, as determined by chromatography (e.g., HPLC). In a completed reaction, the amount of the compound comprising Formula (II) remaining in the reaction mixture may be less than about 3%, and preferably less than about 1%. In general, the reaction may proceed for about 1 hour to about 12 hours, and more typically, for about 2 hours to about 4 hours.

As mentioned above, an advantage of the process is that the compound comprising Formula (III) need not be isolated from the reaction mixture and the compound comprising Formula (III) may be used directly in Step C of the process.

(c) Step C of the Process

The process further comprises contacting the reaction mixture comprising the compound having Formula (III) with carbon dioxide gas to neutralize the excess nucleophile, followed by contact with an N-alkylating agent to form the compound comprising Formula (IV). More specifically, carbon dioxide gas is bubbled through the reaction mixture from step B, wherein the carbon dioxide gas reacts with the nucleophile to form a carbonate compound. As a consequence, the pH of the reaction mixture is adjusted. In embodiments in which the nucleophile is KOH or NaOH, therefore, contact with the carbon dioxide gas converts the KOH or NaOH into $KHCO_3$ or $NaHCO_3$, respectively. The amount of carbon dioxide added to the reaction mixture and the duration of contact can and will vary. In some embodiments, formation of the resultant carbonate compound may be monitored visually (i.e., it precipitates from the reaction mixture). The temperature of the reaction may range from about 0° C. to about 100° C. In preferred embodiments, contact with the carbon dioxide gas may be conducted at room temperature.

Step C of the process further comprises contacting the compound having Formula (III) with an N-alkylating agent comprising $R^{17}X$, wherein $R^{17}$ and X are as defined above. In one embodiment, the N-alkylating agent may be an alkyl halide having from one to ten carbon atoms, or a substituted alkyl halide having from one to ten carbon atoms. In another embodiment, the N-alkylating agent may be an alkenyl halide having from one to ten carbon atoms, or a substituted alkenyl halide having from one to ten carbon atoms. In still another embodiment, the N-alkylating agent may be an aryl halide or a substituted aryl halide. In an alternate embodiment, the N-alkylating agent may be a heterocyclic halide or a substituted heterocyclic halide. In yet another embodiment, the N-alkylating agent may be an alkyl methanesulfonate, or an alkyl p-toluenesulfonate. In preferred embodiments, the N-alkylating agent may be cyclopropylmethyl halide, cyclobutylmethyl halide, allyl halide, or benzyl halide. In exemplary embodiments, the N-alkylating agent may be cyclopropylmethyl bromide, cyclobutylmethyl bromide, allyl bromide, or benzyl bromide.

The amount of N-alkylating agent used in the reaction can and will vary. Typically, the molar ratio of the compound comprising Formula (II) to the N-alkylating agent to may range from about 1:1 to about 1:5. In preferred embodiments, the molar ratio of the compound comprising Formula (II) to the N-alkylating agent may range about 1:1 to about 1:2. In an exemplary embodiment, the molar ratio of the compound comprising Formula (II) to the N-alkylating agent may be about 1:1.1.

The temperature of the alkylation reaction may range from about 0° C. to about 100° C. In preferred embodiments, the reaction may be conducted at a temperature ranging from about 25° C. to about 90° C. In exemplary embodiments, the reaction may be conducted at a temperature ranging from about 50° C. to about 80° C.

The reaction generally is allowed to proceed for a sufficient period of time until the reaction is complete, as determined by chromatography (e.g., HPLC). Typically, the amount of the compound comprising Formula (III) remaining in the reaction mixture upon completion of the reaction may be less than about 3%, and preferably less than about 1%. In general, the reaction may proceed for about 1 hour to about 24 hours, and more typically, for about 2 hours to about 8 hours.

The compound comprising Formula (IV) may be isolated from the reaction mixture using techniques known to those of skill in the art. Non-limiting examples of suitable techniques include precipitation, extraction, evaporation, distillation, chromatography, and crystallization. The compound comprising Formula (IV) may be used as is, or may be converted to another compound using techniques familiar to those of skill in the art.

The yield of the compound comprising Formula (IV) can and will vary. Typically, the yield of the compound comprising Formula (IV) may be at least about 35%. In one embodiment, the yield of the compound comprising Formula (IV) may range from about 35% to about 65%. In another embodiment, the yield of the compound comprising Formula (IV) may range from about 65% to about 75%. In yet another embodiment, the yield of the compound comprising Formula (IV) may range from about 75% to about 85%. In a further embodiment, the yield of the compound comprising Formula (IV) may range from about 85% to about 95%. In still another embodiment, the yield of the compound comprising Formula (IV) may be greater than about 95%.

(d) Stereochemistry

The compounds comprising any of Formulas (I), (II), (III), or (IV) may have a (−) or a (+) orientation with respect to the rotation of polarized light. More specifically, each chiral center of the morphinans may have an R or an S configuration. The compounds described herein may have at least four chiral centers, namely carbons C-5, C-9, C-13, and C-14. At each chiral center, the stereochemistry at the carbon atom is independently R or S. The configuration of C-5, C-9, C-13, and C-14, respectively, may be RRRR, RRRS, RRSR, RSRR, SRRR, RRSS, RSSR, SSRR, SRRS, SRSR, RSRS, RSSS, SRSS, SSRS, SSSR, or SSSS, provided that the C-15 and C-16 atoms are both on the alpha face of the molecule or both on the beta face of the molecule.

The compound comprising any of Formulas (I), (II), (III), or (IV) may be a free base or a pharmaceutically acceptable salt. Pharmaceutically acceptable salts include, without limitation, acetate, aspartate, benzoate, bitartrate, citrate, formate, gluconate, glucuronate, glutamate, fumarate, hydrochloride, hydrobromide, hydroiodide, hypophosphite, isobutyrate, isocitrate, lactate, malate, maleate, meconate, methylbromide, methanesulfonate, monohydrate, mucate, nitrate, oxalate, phenylpriopionate, phosphate, phthalate, propionate, pyruvate, salicylate, stearate, succinate, sulfate, tannate, tartrate, terephthalate, valerate, and the like.

(III) Process for the Preparation of a Compound Comprising Formula (IV) from a Compound Comprising Formula (II)

A further aspect of the invention encompasses a process in which an N-alkyl morphinan comprising Formula (IV) is prepared from an N-hydrocarboxycarbonyl morphinan comprising Formula (II), as detailed above in sections (II)(b) and (c). Briefly, the compound comprising Formula (II) is contacted with a nucleophile to form a nor-morphinan intermediate comprising Formula (III). The process further comprises contacting the compound comprising Formula (III) with carbon dioxide gas, followed by an N-alkylating agent comprising $R^{17}X$ to form the compound comprising Formula (IV).

DEFINITIONS

The compounds described herein have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "oxygen protecting group" as used herein denotes a group capable of protecting an oxygen atom (and hence, forming a protected hydroxy), wherein the protecting group may be removed, subsequent to the reaction for which protection is employed, without disturbing the remainder of the molecule. Exemplary protecting groups include ethers (e.g., allyl, triphenylmethyl (trityl or Tr), p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of protecting groups and the synthesis thereof may be found in "Protective Groups in Organic Synthesis" by T. W. Greene and P. G. M. Wuts, $3^{rd}$ ed., John Wiley & Sons, 1999.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples are included to demonstrate preferred embodiments of the invention. It should be appreciated by those of skill in the art that the techniques disclosed in the examples represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth is to be interpreted as illustrative and not in a limiting sense.

Example 1

Synthesis of 17-phenylcarbomatyl-4,5-epoxy-3-methoxy-cyclic 1,2-ethanediyl acetal-(5α)-morphinan-6-one—Trial 1

The following reaction scheme depicts the demethylation reaction:

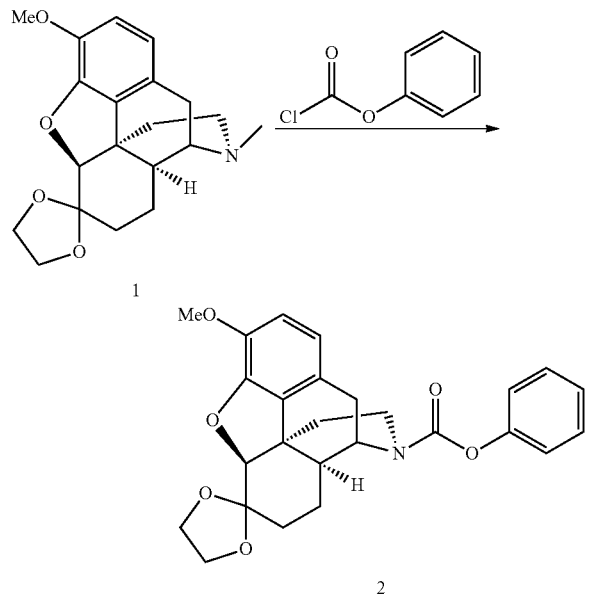

A mixture of 17-methyl-4,5-epoxy-3-methoxy-cyclic 1,2-ethanediyl acetal-(5α)-morphinan-6-one 1 (32.4 g), sodium bicarbonate(23.8 g), and chloroform (145 mL) was prepared in an ice bath (and cooled for 10 min). To the cooled mixture was added phenyl chloroformate dropwise. The resulting mixture was gradually heated to 53° C. for two hours. HPLC analysis indicated the reaction was complete. The mixture was filtered. The solid was washed with $CHCl_3$ (2×20 mL). The solution was added to ice-cooled 5% $Na_2CO_3$ (145 mL). The organic phase was separated and the aqueous phase was extracted with $CHCl_3$ (2×60 mL). The combined organic phases were washed with water (2×100 mL). The organic layer was evaporated on rotar-vapor and gave a foam solid, 44.7 g crude material. Part of the crude product (29.7 g) was re-crystallized from a mixture of isopropanol (297 mL) and heptane (130 mL), to provide 28 g of white solid product 2 (yield=99%; purity=97%). MS(ESP): MW+1=450.0.

Example 2

Synthesis of 17-phenylcarbomatyl-4,5-epoxy-3-methoxy-cyclic 1,2-ethanediyl acetal-(5α)-morphinan-6-one—Trial 2

A mixture of 17-methyl-4,5-epoxy-3-methoxy-cyclic 1,2-ethanediyl acetal-(5α)-morphinan-6-one 1 (1.0 g), sodium bicarbonate (0.74 g), and ethyl acetate (5 mL) was cooled in ice bath for 10 min. To the cooled mixture was added phenyl chloroformate (0.44 mL) dropwise. The resulting mixture was gradually heated to 50° C. for three hours. After cooling to room temperature, 5 mL of water was added to the reaction mixture and the phases were allowed to separate. The organic phase was removed, and the aqueous phase was extracted with ethyl acetate (2×5 mL). The combined organic phases were washed with 1.0 N sodium hydroxide solution (2×5 m), 2.5% HCl solution (2×5 mL), and then dried over anhydrous sodium sulfate. After filtering over drying agent, the filtrate was evaporated in vacuo and gave 1.3 g, purity=82%.

Example 3

Synthesis of 17-(cyclobutylmethyl)-4,5-epoxy-3-methoxy-cyclic 1,2-ethanediyl acetal-(5α)-morphinan-6-one The N-alkyl compound was prepared according to the following reaction scheme:

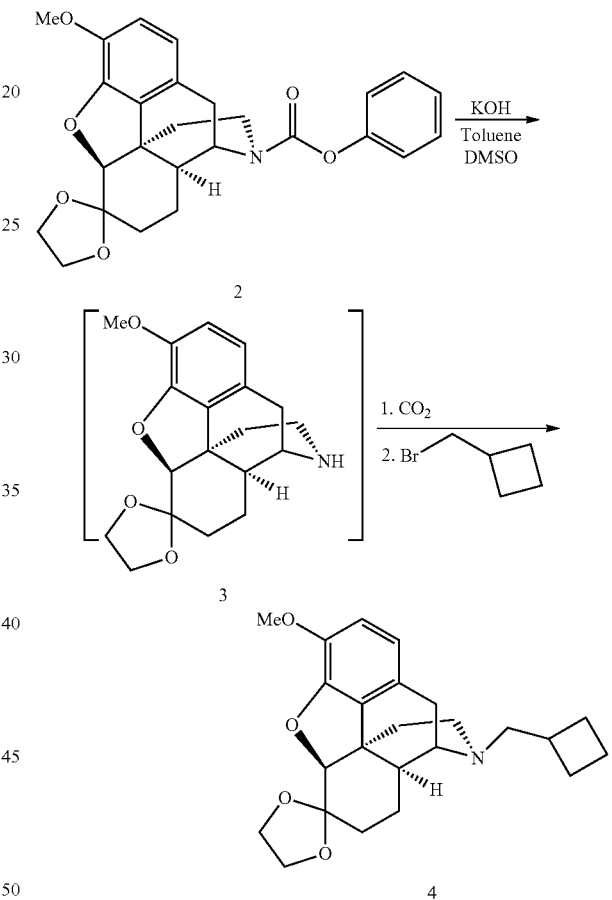

A mixture of 17-phenylcarbomatyl-4,5-epoxy-3-methoxy-cyclic 1,2-ethanediyl acetal-(5α)-morphinan-6-one 2 (1 g), toluene (4 mL), DMSO (1 mL), and powdered KOH (0.5 g) was prepared under nitrogen and heated to 86° C. (in an oil bath) for two hrs. HPLC monitoring of the reaction indicated that the reaction was complete. The reaction mixture was cooled to room temperature. Carbon dioxide was bubbled through the reaction mixture for 10 min, and plenty of white precipitate was formed. To the reaction mixture was added 2 mL dry DMF, followed by the addition of bromomethylcyclobutane (0.27 mL). The resulting mixture was heated at 75° C. overnight. After HPLC monitoring indicated that the reaction was done, the mixture was cooled to room temperature. To the reaction mixture was added 80 mL ethyl acetate, and the resulting organic phase was separated and washed with 3.0 N sodium hydroxide aqueous solution until the phenol was removed completely. The organic phase was then washed with brine and dried over anhydrous sodium sulfate. After removing the organic volatiles, 0.75 g of product 4 was obtained as a white solid (yield=86%).

Example 4

Synthesis of 17-(cyclopropylmethyl)-4,5-epoxy-3-methoxy-cyclic 1,2-ethanediyl acetal-(5α)-morphinan-6-one The cyclopropylmethyl derivative was prepared according to the following reaction scheme:

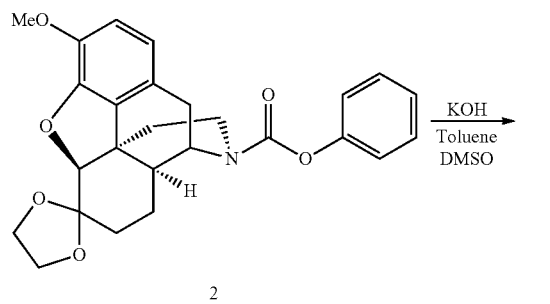

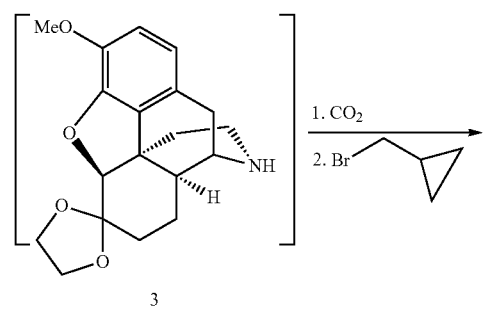

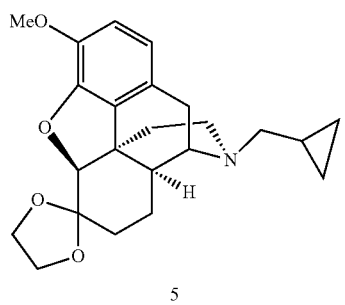

A mixture of 17-phenylcarbomatyl-4,5-epoxy-3-methoxy-cyclic 1,2-ethanediyl acetal-(5α)-morphinan-6-one 2 (10 g), toluene (43 mL), DMSO (11 mL), and powdered KOH (5 g) was prepared under nitrogen and heated to 86° C. (in an oil bath) for two hrs. HPLC monitoring indicated that the reaction was done. The reaction mixture was cooled to room temperature. Carbon dioxide was bubbled through the reaction mixture for 10 min, wherein a white precipitate was formed. To the reaction mixture was added 23 mL of NMP, and then bromomethylcyclobutane (2.37 mL). The resulting mixture was heated at 60° C. for three hrs. After HPLC monitoring indicated that the reaction was done, the mixture was cooled to room temperature. To the reaction mixture was added 400 mL ethyl acetate/DCM (8:1), and the resulting organic phase was separated and washed with 1.0 N sodium hydroxide aqueous solution until the phenol was removed completely. The organic phase was then washed with brine and dried over anhydrous sodium sulfate. After removal of the volatiles, 8 g of light brown oil was obtained.

Example 5

Synthesis of N-phenoxycarbonyl dihydrothebaine

Dihydrothebaine was demethylated according to the following reaction scheme:

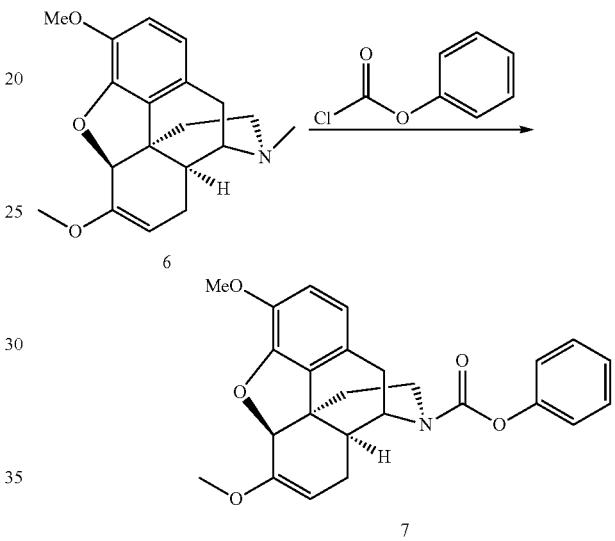

A mixture of dihydrothebaine 6 (30 g), sodium bicarbonate (24.2 g) and 216 mL of acetonitrile was prepared in an ice bath and phenylchloroformate (18 mL) was added dropwise. The reaction was then gradually heated to 50° C. (in an oil bath) for two hrs. The reaction was cooled to 0° C. in ice bath for 10 min, and another 4.8 g sodium bicarbonate added, followed by addition of another 6 mL phenyl chloroformate. The reaction was heated to 50° C. degree, and HPLC monitoring after three hr indicated that the reaction was finished. The reaction mixture was cooled to room temperature, and 500 mL ethyl acetate and 200 mL water were added. The organic phase was separated and washed with 2 N sodium hydroxide (4×150 mL), water (200 mL), and 5% formic acid solution (2×60 mL) and brine, and then dried over anhydrous magnesium sulfate. After removal of the volatiles, the product phenyl nordihydrothebaine carbonate 7 was obtained as a light purple solid (42 g), with a quantitative yield and purity=88%.

Example 6

Synthesis of 17-(cyclopropanylmethyl)-4,5-epoxy-3-methoxy-6-methoxy-(5α)-morphinan-6-ene The following reaction scheme depicts the preparation of the cyclopropyl derivative:

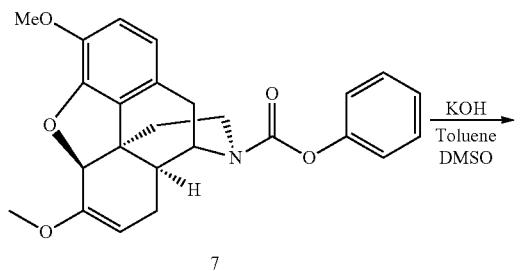
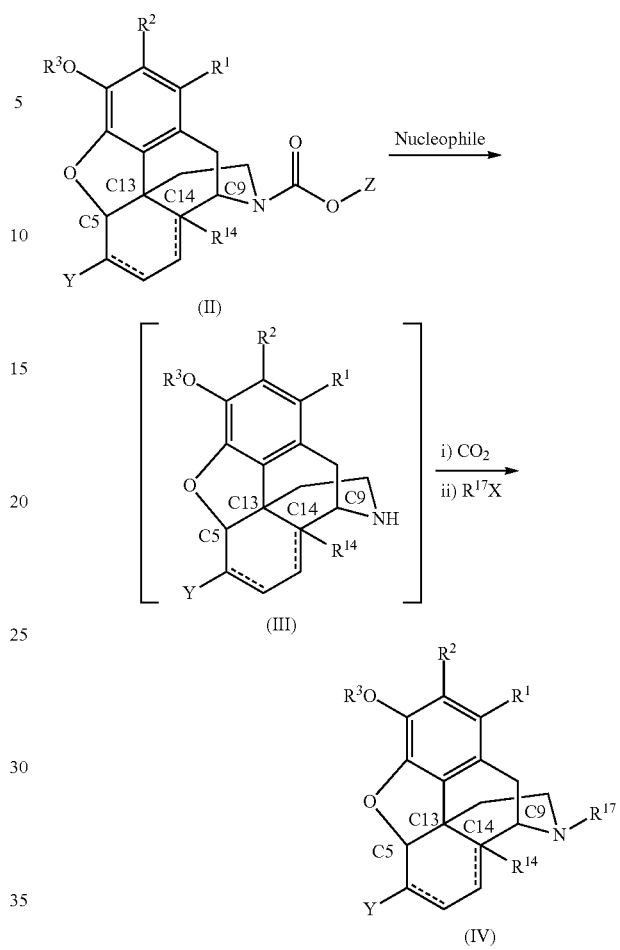

A mixture of N-phenoxycarbonyl dihydrothebaine 7 (6.7 g), toluene (29 mL), dimethyl sulfoxide (7.3 mL) and powdered potassium hydroxide (3.6 g, 0.064 mole, 4. eqv) was heated to 86° C. (in an oil bath). The reaction was monitored with HPLC. After two hrs, the reaction mixture was then cooled to room temperature, and dry carbon dioxide was bubbled through the reaction mixture for 20 min, wherein a white precipitates was formed. To the reaction mixture was added 15 ml of dry NMP, and then 1.7 mL bromomethyl-cyclopropane. The resulting mixture was heated to 60° C. (in an oil bath) for three hrs; the reaction mixture was held at room temperature overnight. To the reaction mixture was added 200 mL ethyl acetate and 100 mL water. The organic phase was separated, washed with 2N sodium hydroxide (4×50 mL) and water (100 mL), and then dried over sodium sulfate. After removal of the volatiles, 4.6 g of product 9 was obtained as sticky glossy material.

What is claimed is:

1. A one pot process for preparing a compound represented by Formula (IV) from a compound represented by Formula (II), the process comprising:
   a) contacting the compound represented by Formula (II) with a nucleophile to form a compound represented by Formula (III); and
   b) contacting the compound represented by Formula (III) with carbon dioxide gas followed by an N-alkylating agent comprising $R^{17}X$ to form the compound represented by Formula (IV);

wherein:
$R^1$ and $R^2$ are independently chosen from hydrogen, halogen, hydroxy, amino, cyano, {—}$OR^8$, hydrocarbyl, and substituted hydrocarbyl;
$R^3$ is chosen from hydrogen, hydrocarbyl, and substituted hydrocarbyl;
$R^{14}$ is chosen from hydrogen, halogen, hydroxy, {—}$OR^8$, hydrocarbyl, and substituted hydrocarbyl;
$R^8Z$ are independently chosen from hydrocarbyl and substituted hydrocarbyl;
$R^{17}$ is chosen from cycloalkyls, allyls, and benzyls;
X is a leaving group;
Y is chosen from hydroxy, alkoxy, aryloxy, and acetal, wherein each dashed line indicates an optional double bond; and
the nucleophile is chosen from potassium hydroxide, sodium hydroxide, magnesium hydroxide, calcium hydroxide, potassium carbonate, and sodium carbonate.

2. The process of claim 1, wherein:
$R^1$, $R^2$, and $R^{14}$ are independently chosen from hydrogen, halogen, hydroxy, alkyoxy, acyl, alkyl, alkenyl, aryl, substituted alkyl, substituted alkenyl, substituted aryl, alkoxycarbonyl, and aroxycarbonyl;
$R^3$ is chosen from hydrogen, alkyl, alkenyl, aryl, substituted alkyl, substituted alkenyl, substituted aryl, acyl, alkoxycarbonyl, aroxycarbonyl, acetal, ether, silyl ether, and alkylsulfonyl;

Z is chosen from alkyl, alkenyl, alkylaryl, aralkyl, aryl, substituted alkyl, substituted alkenyl, substituted alkylaryl, substituted aralkyl, and substituted aryl;

X is halogen or $SO_2OR$, wherein R is alkyl, aryl, substituted alkyl, or substituted aryl; and Y is methoxy, ethoxy, or ethylene acetal.

3. The process of claim 1, wherein the compound represented by Formula (III) is not isolated; the nucleophile is chosen from an amide, an alkoxide, a hydride, alkali metal hydroxides, and alkaline earth metal hydroxides; the molar ratio of the compound represented by Formula (II) to the nucleophile is from 1:1 to 1:8; the N-alkylating agent is chosen from an alkyl halide, an alkenyl halide, an aryl halide, an alkyl methanesulfonate, and an alkyl p-toluenesulfonate; the molar ratio of the compound represented by Formula (II) to the N-alkylating agent is from 1:1 to 1:2; the process is conducted in the presence of a solvent system comprising a nonpolar organic solvent chosen from toluene and chlorobenzene and combinations thereof; the molar ratio of the nonpolar solvent to the compound represented by Formula (II) is from 0.5:1 to 20:1; and the process is conducted at a temperature from 0° C. to 100° C.

4. The process of claim 3, wherein the solvent system further comprises a protic solvent chosen from water, methanol, ethanol, isopropyl alcohol, isobutyl alcohol, t-butyl alcohol, n-propyl alcohol, n-butyl alcohol, and combinations thereof.

5. The process of claim 3, wherein the solvent system further comprises an aprotic solvent chosen from acetonitrile, 1-methyl-2-pyrrolidinone, N,N-dimethylacetamide, dimethyl sulfoxide, N,N-formamide, and combinations thereof; and the volume ratio of the aprotic solvent to the nonpolar solvent is from 1:1 to 1:10.

6. The process of claim 2, wherein the nucleophile is potassium hydroxide or sodium hydroxide; the molar ratio of the compound represented by Formula (II) to the nucleophile is 1:4.1; the N-alkylating agent is chosen from cyclopropylmethyl halide, cyclobutylmethyl halide, allyl halide, and benzyl halide; the molar ratio of the compound represented by Formula (II) to the N-alkylating agent is 1:1.1; the process is conducted in the presence of a solvent system comprising toluene and dimethyl sulfoxide; the molar ratio of toluene to the compound represented by Formula (II) is 4:1; the volume ratio of toluene to dimethyl sulfoxide is 5:1; the process is conducted at a temperature from 60° C. to 90° C.; and the compound represented by Formula (IV) has a yield of at least 50%.

7. The process of claim 1, wherein the optical activity of the compounds represented by Formulas (II), (III), and (IV) is chosen from (−) enantiomer, (+) enantiomer, and combinations thereof; and the configuration of C-5, C-13, C-14, and C-9, respectively, is chosen from RRRR, RRRS, RRSR, RSRR, SRRR, RRSS, RSSR, SSRR, SRRS, SRSR, RSRS, RSSS, SRSS, SSRS, SSSR, and SSSS, provided that C-15 and C-16 are both either on the alpha face or the beta face of the molecule.

8. A one pot process for preparing a compound represented by Formula (IV) from a compound represented by Formula (I), the process comprising:
 a) contacting the compound represented by Formula (I) with an N-demethylating agent comprising LC(O)OZ and a proton acceptor to form a compound represented by Formula (II);
 b) contacting the compound represented by Formula (II) with a nucleophile to form a compound represented by Formula (III); and
 c) contacting the compound represented by Formula (III) with carbon dioxide gas followed by an N-alkylating agent comprising $R^{17}X$ to form the compound represented by Formula (IV);

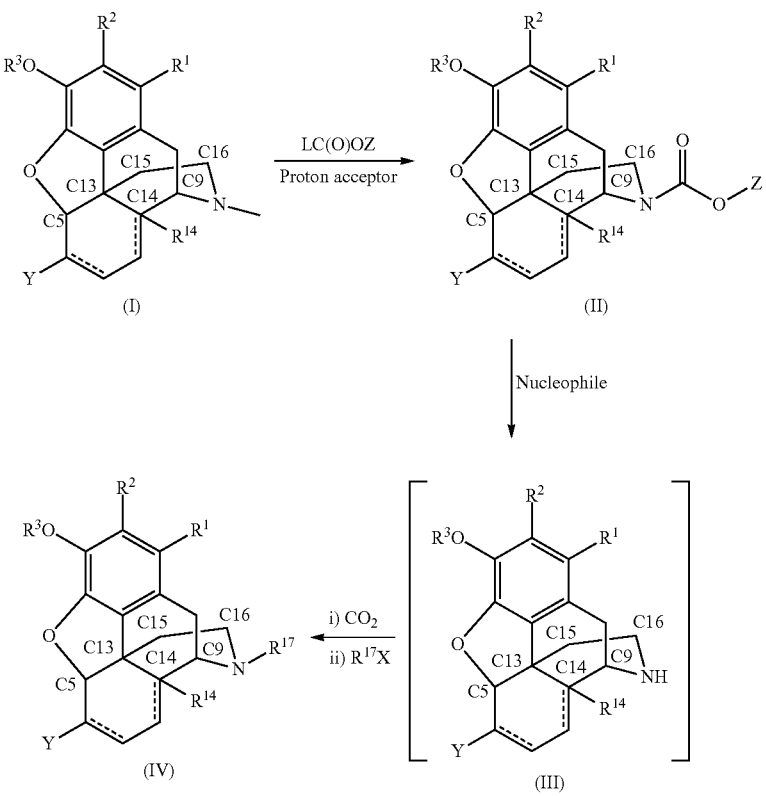

wherein:
R¹ and R² are independently chosen from hydrogen, halogen, hydroxy, amino, cyano, {—}OR⁸, hydrocarbyl, and substituted hydrocarbyl;
R³ is chosen from hydrogen, hydrocarbyl, and substituted hydrocarbyl;
R¹⁴ is chosen from hydrogen, halogen, hydroxy, {—}OR⁸, hydrocarbyl, and substituted hydrocarbyl;
R⁸Z are independently chosen from hydrocarbyl and substituted hydrocarbyl;
R¹⁷ is chosen from cycloalkyls, allyls, and benzyls;
L is halogen;
X is a leaving group;
Y is chosen from hydroxy, alkoxy, aryloxy, and acetal, wherein each dashed line indicates an optional double bond; and
the nucleophile is chosen from potassium hydroxide, sodium hydroxide, magnesium hydroxide, calcium hydroxide, potassium carbonate, and sodium carbonate.

9. The process of claim 8, wherein:
R¹, R², and R¹⁴ are independently chosen from hydrogen, halogen, hydroxy, alkyoxy, acyl, alkyl, alkenyl, aryl, substituted alkyl, substituted alkenyl, substituted aryl, alkoxycarbonyl, and aroxycarbonyl;
R³ is chosen from hydrogen, alkyl, alkenyl, aryl, substituted alkyl, substituted alkenyl, substituted aryl, acyl, alkoxycarbonyl, aroxycarbonyl, acetal, ether, silyl ether, and alkylsulfonyl;
Z is chosen from alkyl, alkenyl, alkylaryl, aralkyl, aryl, substituted alkyl, substituted alkenyl, substituted alkylaryl, substituted aralkyl, and substituted aryl;
X is halogen or $SO_2OR$, wherein R is alkyl, aryl, substituted alkyl, or substituted aryl; and
Y is methoxy, ethoxy, or ethylene acetal.

10. The process of claim 8, wherein the N-demethylating agent is chosen from an alkyl haloformate, an alkoxyalkyl haloformate, benzyl haloformate, phenyl haloformate, vinyl haloformate, and 2-chloroalkyl haloformate; the proton acceptor has a pKa greater than 7 and is chosen from $NaHCO_3$, $KHCO_3$, $Na_2CO_3$, $K_2CO_3$, NaOH, KOH, and combinations thereof; the molar ratio of the compound represented by Formula (I) to the N-demethylating agent to the proton acceptor is from 1:1:1 to 1:3:6; the molar ratio of the compound represented by Formula (II) to the N-alkylating agent is from 1:1 to 1:2; and the compound represented by Formula (III) is not isolated.

11. The process of claim 8, wherein the reaction of step (a) is conducted in the presence of a solvent chosen from benzene, chloroform, diethyl ether, ethyl acetate, n-propyl acetate, heptane, hexane, toluene, acetonitrile, 1-methyl-2-pyrrolidinone, N,N-dimethylacetamide, dimethyl sulfoxide, N,N-formamide, acetone, tetrahydrofuran, and combinations thereof; the molar ratio of the solvent to the compound represented by Formula (I) is from 0.5:1 to 20:1; the reaction of step (a) is conducted at a temperature from 0° C. to 60° C.; the reactions of steps (b) and (c) are conducted in the presence of a solvent system comprising a nonpolar organic solvent chosen from toluene and chlorobenzene and combinations thereof; the molar ratio of the nonpolar solvent to the compound represented by Formula (II) is from 0.5:1 to 20:1; and the reactions of steps (b) and (c) are conducted at a temperature from 0° C. to 100° C.

12. The process of claim 11, wherein the solvent system further comprises a protic solvent chosen from water, methanol, ethanol, isopropyl alcohol, isobutyl alcohol, t-butyl alcohol, n-propyl alcohol, n-butyl alcohol, and combinations thereof.

13. The process of claim 11, wherein the solvent system further comprises an aprotic solvent chosen from acetonitrile, 1-methyl-2-pyrrolidinone, N,N-dimethylacetamide, dimethyl sulfoxide, N,N-formamide, and combinations thereof; and the volume ratio of the aprotic solvent to the nonpolar solvent is from 1:1 to 1:10.

14. The process of claim 8, wherein the N-demethylating agent is an alkyl chloroformate or phenyl chloroformate; the proton acceptor is $NaHCO_3$ or $KHCO_3$; the molar ratio of the compound represented by Formula (I) to the N-demethylating agent to the proton acceptor is from 1:1:1.5 to 1:3:3; the reaction of step (a) is conducted at a temperature from 0° C. to 60° C. and in the presence of a solvent chosen from chloroform or acetonitrile; the molar ratio of the solvent to the compound represented by Formula (I) is from 2:1 to 10:1; the nucleophile is potassium hydroxide or sodium hydroxide; the molar ratio of the compound represented by Formula (II) to the nucleophile is 1:4.1; the N-alkylating agent is chosen from cyclopropylmethyl halide, cyclobutylmethyl halide, allyl halide, and benzyl halide; the molar ratio of the compound represented by Formula (II) to the N-alkylating agent is 1:1.1; the reactions of steps (b) and (c) are conducted at a temperature from 60° C. to 90° C. and in the presence of a solvent system comprising toluene and dimethyl sulfoxide; the molar ratio of toluene to the compound represented by Formula (II) is 4:1; and the volume ratio of toluene to dimethyl sulfoxide is 5:1.

15. The process of claim 8, wherein the optical activity of the compounds represented by Formulas (I), (II), (III), and (IV) is chosen from (−) enantiomer, (+) enantiomer, and combinations thereof; and the configuration of C-5, C-13, C-14, and C-9, respectively, is chosen from RRRR, RRRS, RRSR, RSRR, SRRR, RRSS, RSSR, SSRR, SRRS, SRSR, RSRS, RSSS, SRSS, SSRS, SSSR, and SSSS, provided that C-15 and C-16 are both either on the alpha face or the beta face of the molecule.

* * * * *